United States Patent
Hum et al.

(10) Patent No.: US 10,626,454 B2
(45) Date of Patent: Apr. 21, 2020

(54) COMPOSITIONS AND METHODS FOR NUCLEIC ACID AMPLIFICATION AND ANALYSIS

(71) Applicant: SeqMatic, LLC, Fremont, CA (US)

(72) Inventors: Victor Hum, Fremont, CA (US); Danny Lee, Fremont, CA (US); Kelvin Chan, Fremont, CA (US)

(73) Assignee: SeqMatic, LLC, Fremont, CA (US)

( * ) Notice: Subject to any disclaimer, the term of this patent is extended or adjusted under 35 U.S.C. 154(b) by 205 days.

(21) Appl. No.: 15/660,895

(22) Filed: Jul. 26, 2017

(65) Prior Publication Data

US 2018/0030511 A1 Feb. 1, 2018

Related U.S. Application Data

(60) Provisional application No. 62/367,613, filed on Jul. 27, 2016.

(51) Int. Cl.
*C12Q 1/68* (2018.01)
*C12Q 1/686* (2018.01)
*C12Q 1/6816* (2018.01)

(52) U.S. Cl.
CPC ........... *C12Q 1/686* (2013.01); *C12Q 1/6816* (2013.01)

(58) Field of Classification Search
CPC .............. C12Q 1/686; C12Q 2525/125; C12Q 2525/137
See application file for complete search history.

(56) References Cited

U.S. PATENT DOCUMENTS 5,487,972 A 1/1996 Gelfand et al.
6,962,780 B2 11/2005 Nakayama et al.
2002/0058258 A1 5/2002 Wittwer et al.
2009/0148933 A1* 6/2009 Battrell ............... B01F 11/0071
  435/287.2
2012/0028259 A1 2/2012 Zhang et al.

OTHER PUBLICATIONS

Burckhardt, J. Amplification of DNA from whole blood. Genome Research (1994) 3:239-243.*
Saiki, et al., Primer-Directed Enzymatic Amplification of DNA with a Thermostable DNA Polymerase, Jan. 1998, pp. 487-491. 0.
Enzymatic Amplification of DNA by PCR: Standard Procedures and Optimization, Current Protocols in Molecular Biology, 2001.
Seqmatic, TailorMix HT1 qPCR Kit, Aug. 2015, 4 pages.
Sequencing Library qPCR Quantification, Illumina Proprietary, Feb. 2011, 28 Pages.
Higuchi, et al., Kinetic PCR Analysis: Real-time Monitoring of DNA Amplification Reactions, Technology, Sep. 1993, 11:1026-30.
Innis, et al., Optimization of PCRs, PCR Protocols: A Guide to Methods and Applications, 1990.
Meyer, et al., From micrograms to picograms: quantitative PCR reduces the material demands of high-throughput sequencing, Nucleic Acids Research, 2008, vol. 36, No. 1, 6 pages.
Zhang, et al., Direct DNA Amplification from Crude Clinical Samples Using a PCR Enhancer Cocktail and Novel Mutants of Taq, Journal of Molecular Diagnostics, Mar. 2010, 12(2):152-61.

* cited by examiner

*Primary Examiner* — David C Thomas
(74) *Attorney, Agent, or Firm* — Wilson Sonsini Goodrich & Rosati

(57) ABSTRACT

The present disclosure provides compositions and methods for nucleic acid amplification and analysis. In some embodiments, a nucleic acid amplification reaction mixture is formulated to minimize or eliminate the inclusion of a species that can affect activity of one or more inhibitory species in the nucleic acid amplification reaction mixture. Such reaction mixtures can permit suitable analysis of nucleic acid sample prior to their use in one or more downstream assays, including nucleic acid sequencing assays.

29 Claims, 9 Drawing Sheets

FIG. 4A PCR mix composition, 10% glycerol with 1x Eva

| Reagent Component | Final Conc. (2x) |
|---|---|
| Tris pH 8.8 | 134mM |
| MgCl$_2$ | 4mM |
| dNTP mix | 0.4mM |
| EvaGreen Dye | 1x |
| Ammonium sulfate, (NH4)2SO4 | 33.2mM |
| Glycerol | 20% |
| Taq | 0.1U/ul |

| Sample Conc. (pM) | Ct value |
|---|---|
| 25 | 12.53 |
| 10 | 13.77 |
| 1 | 16.86 |
| 0.1 | 20.71 |
| 0.01 | 23.76 |

COMPOSITIONS AND METHODS FOR NUCLEIC ACID AMPLIFICATION AND ANALYSIS

CROSS-REFERENCE

This application claims the benefit of U.S. Provisional Application No. 62/367,613, filed Jul. 27, 2016, which is incorporated herein by reference in its entirety.

BACKGROUND

Nucleic acid sequencing techniques are widely used in biological applications, for a variety of different sample types. Indeed, sequencing techniques, including those considered "next-generation" have substantial utility in forensics, diagnostics and other application. Next-generation sequencing methods are expensive, though, with a single analysis often running on the order of several thousand or several tens of thousands of dollars. It can be helpful to measure the template content of a sequencing preparation prior to providing it to a sequencing instrument for analysis, so that optimum sequencing parameters can be met. Ascertaining an amount of template in a preparation to be subject to sequencing can avoid sequencing errors, minimize waste and help improve the quality of sequencing reads that are obtained during sequencing. Many sequencing preparations utilize reagents that contain inhibitors that inhibit quantitative nucleic acid analysis suitable for quantifying the amount of template in a sequencing reaction preparation, including quantitative polymerase chain reaction (qPCR).

SUMMARY

Recognized herein is the considerable unmet need for compositions and methods useful in quantifying nucleic acids in sample preparations, including those samples prepared for nucleic acid sequencing.

In one aspect, a method is provided for amplifying one or more template nucleic acids present in a sample, the method comprising: (a) providing a nucleic acid amplification reaction mixture comprising: (i) the one or more template nucleic acids; (ii) reagents necessary for conducting a nucleic acid amplification reaction; and (iii) citrate and sodium chloride; and (b) performing the nucleic acid amplification reaction with the nucleic acid amplification reaction mixture under conditions to yield amplified products of the one or more template nucleic acids. In some cases, the citrate is sodium citrate. In some cases, the nucleic acid amplification reaction mixture comprises from about 3 millimolar (mM) to about 300 mM sodium citrate. In some cases, the nucleic acid amplification reaction mixture comprises from about 30 mM to about 3 molar (M) sodium chloride. In some cases, the nucleic acid amplification reaction mixture comprises from about 0.15 mM to about 15 mM sodium citrate. In some cases, the nucleic acid amplification reaction mixture comprises from about 1.5 mM to about 150 mM sodium chloride. In some cases, the nucleic acid amplification reaction mixture comprises less than about 10 mM potassium salt. In some cases, the nucleic acid amplification reaction mixture is substantially free of potassium salt. In some instances, the potassium salt is potassium chloride. In some cases, the nucleic acid amplification reaction mixture comprises ammonium salt. In some cases, the ammonium salt is ammonium sulfate or ammonium chloride. In some cases, the nucleic acid amplification reaction mixture is substantially free of ammonium salt. In some examples, the nucleic acid amplification reaction mixture comprises less than about 30 mM ammonium salt. In some cases, the performing the nucleic acid amplification reaction comprises performing polymerase chain reaction (PCR). In some instances, the PCR is quantitative PCR (qPCR). In some cases, the method further comprises determining a concentration of the one or more template nucleic acids present in the sample. In some cases, the sample comprises citrate, sodium chloride or both and is directly introduced to the nucleic acid amplification reaction mixture without prior processing to a lower concentration of citrate, sodium chloride or both. In some cases, the nucleic acid amplification reaction mixture comprises HT1 buffer. In some cases, the performing the nucleic acid amplification reaction comprises: (i) denaturing the one or more template nucleic acids thereby generating one or more denatured template nucleic acids; (ii) annealing a primer to the one or more denatured template nucleic acids; (iii) extending the primer to generate one or more extended nucleic acids; and (iv) repeating (i)-(iii) using the one or more extended nucleic acids as templates, thereby generating the amplified products. In some examples, the amplification reaction mixture further comprises a nucleic acid detection agent yielding a detectable signal that is indicative of a presence of the amplified products. In some instances, the amplification reaction mixture further comprises a nucleic acid detection agent yielding a detectable signal, wherein an intensity of the detectable signal is proportional to an amount of the amplified products. In some cases, the method further comprises detecting the amplified products at a cycle threshold ($C_t$) of less than 35 cycles. In some cases, the citrate, sodium chloride, or both is present in the nucleic acid amplification reaction mixture in an amount that would otherwise inhibit the nucleic acid amplification reaction. In some cases, the citrate, sodium chloride, or both is present in the nucleic acid amplification reaction mixture in an amount that would otherwise inhibit the nucleic acid amplification reaction when performed in a nucleic acid amplification reaction mixture containing more than 10 mM potassium chloride. In some cases, the reagents necessary for conducting a nucleic acid amplification reaction comprise a polymerase, nucleotides or analogues thereof, and primers to effect template-directed nucleic acid amplification. In some examples, the nucleic acid amplification reaction mixture comprises from about 0.5 mM to about 20 mM $MgCl_2$. In some examples, the nucleic acid amplification reaction mixture comprises from about 0.05 mM to about 1.0 mM nucleotides or analogues thereof. In some examples, the nucleic acid amplification reaction mixture further comprises less than about 0.5% volume-per-volume (v/v) detergent. In some cases, the nucleic acid amplification reaction mixture further comprises less than about 15% v/v organic solvent. In some cases, the nucleic acid amplification reaction mixture further comprises less than about 20% v/v glycerol. In some instances, the nucleic acid amplification reaction mixture further comprises from about 500 mM to about 5 M of a betaine. In some instances, the nucleic acid amplification reaction mixture has a pH from about 7.0 to about 9.5. In some cases, the one or more template nucleic acids comprises a library of nucleic acids. In some cases, the one or more template nucleic acids are deoxyribonucleic acid (DNA).

In another aspect, a method is provided for amplifying one or more template nucleic acids present in a sample, the method comprising: (a) providing a nucleic acid amplification reaction mixture comprising: (i) the one or more template nucleic acids; (ii) reagents necessary for conducting a nucleic acid amplification reaction; and (iii) less than about 10 mM potassium salt, wherein the nucleic acid amplification reaction mixture is substantially free of ammonium salt; and (b) performing the nucleic acid amplification reaction with the nucleic acid amplification reaction mixture under conditions to yield amplified products of the one or more template nucleic acids. In some cases, the performing the nucleic acid amplification reaction comprises: (i) denaturing the one or more template nucleic acids thereby generating one or more denatured template nucleic acids; (ii) annealing a primer to the one or more denatured template nucleic acids; (iii) extending the primer to generate one or more extended nucleic acids; and (iv) repeating (i)-(iii) using one or more extended nucleic acids as templates, thereby generating the amplified products. In some cases, the nucleic acid amplification reaction mixture comprises citrate, sodium chloride or both. In some cases, the nucleic acid amplification reaction mixture comprises sodium citrate. In some instances, the nucleic acid amplification reaction mixture comprises from about 3 mM to about 300 mM sodium citrate. In some instances, the nucleic acid amplification reaction mixture comprises from about 30 mM to about 3 M sodium chloride. In some instances, the nucleic acid amplification reaction mixture comprises from about 0.15 mM to about 15 mM sodium citrate. In some instances, the nucleic acid amplification reaction mixture comprises from about 1.5 mM to about 150 mM sodium chloride. In some cases, the one or more template nucleic acids comprises a library of nucleic acids. In some cases, the one or more template nucleic acids are DNA or RNA. In some cases, the potassium salt is potassium chloride. In some examples, the nucleic acid amplification reaction mixture is substantially free of potassium salt. In some cases, the ammonium salt is ammonium sulfate or ammonium chloride. In some instances, the nucleic acid amplification reaction mixture comprises from about 0.5 mM to about 20 mM $MgCl_2$. In some instances, the nucleic acid amplification reaction mixture comprises from about 0.05 mM to about 1 mM nucleotides or analogues thereof. In some instances, the nucleic acid amplification reaction mixture further comprises less than about 0.5% v/v detergent. In some instances, the nucleic acid amplification reaction mixture further comprises less than about 15% v/v organic solvent. In some instances, the nucleic acid amplification reaction mixture further comprises less than about 20% v/v glycerol. In some examples, the nucleic acid amplification reaction mixture further comprises from about 500 mM to about 5 M of a betaine. In some instances, the nucleic acid amplification reaction mixture has a pH from about 7.0 to about 9.5. In some cases, the performing nucleic acid amplification reaction comprises performing polymerase chain reaction (PCR). In some examples, the PCR is quantitative PCR (qPCR). In some cases, the method further comprises determining a concentration of the one or more template nucleic acids present in the sample. In some cases, the nucleic acid amplification reaction mixture comprises HT1 buffer. In some cases, the nucleic acid amplification reaction mixture further comprises a nucleic acid detection agent yielding a detectable signal that is indicative of a presence of the amplified products. In some cases, the nucleic acid amplification reaction mixture further comprises a nucleic acid detection agent yielding a detectable signal, wherein an intensity of the detectable signal is proportional to an amount of the amplified products. In some cases, the method further comprises detecting the amplified products at a cycle threshold ($C_t$) of less than 35 cycles. In some cases, the citrate, sodium chloride, or both is present in the nucleic acid amplification reaction mixture in an amount that would otherwise inhibit the nucleic acid amplification reaction. In some cases, the citrate, sodium chloride, or both is present in the nucleic acid amplification reaction mixture in an amount that would otherwise inhibit the nucleic acid amplification reaction when performed in a nucleic acid amplification reaction mixture containing more than 10 mM potassium chloride.

In another aspect, a method is provided for conducting a nucleic acid sequencing assay, the method comprising: (a) quantifying an amount of template nucleic acids in a sample to be sequenced by performing a quantitative polymerase chain reaction (qPCR) in a nucleic acid amplification reaction mixture, wherein the qPCR directly utilizes the template nucleic acids present in the sample, wherein the reaction mixture contains citrate, sodium chloride, or both; and (b) subjecting an appropriate amount of the template nucleic acids present in the sample based on the quantifying of (a) to the nucleic acid sequencing assay, thereby conducting the nucleic acid sequencing assay. In some cases, the qPCR directly utilizes the template nucleic acids such that the template nucleic acids in the sample are not processed to lower concentration of sodium citrate, sodium chloride, or both in the sample prior to the qPCR. In some instances, the citrate is sodium citrate. In some cases, the sample comprises a hybridization buffer. In some examples, the hybridization buffer is HT1 buffer. In some cases, the citrate, sodium chloride, or both is present in an amount that would otherwise inhibit quantitative polymerase chain reaction (qPCR). In some cases, the citrate, sodium chloride, or both is present in an amount that would otherwise inhibit quantitative polymerase chain reaction (qPCR) when performed in a nucleic acid amplification reaction mixture containing more than 10 mM potassium chloride. In some cases, the nucleic acid amplification reaction mixture comprises less than about 10 mM potassium salt. In some cases, the nucleic acid amplification reaction mixture is substantially free of an ammonium salt. In some cases, the subjecting comprises hybridizing the appropriate amount of the template nucleic acids to one or more probes immobilized on a solid support. In some cases, the method further comprises amplifying the appropriate amount of the template nucleic acids on the solid support thereby generating amplified immobilized nucleic acids. In some cases, the method further comprises performing a sequencing-by-synthesis reaction on the amplified immobilized nucleic acids.

In yet another aspect, a method is provided for conducting a nucleic acid sequencing assay, the method comprising: (a) quantifying an amount of template nucleic acids in a sample to be sequenced by performing a quantitative polymerase chain reaction (qPCR) in a nucleic acid amplification reaction mixture, wherein the nucleic acid amplification reaction mixture comprises less than about 10 mM potassium salt and wherein the nucleic acid amplification reaction mixture is substantially free of ammonium salt; (b) subjecting an appropriate amount of the template nucleic acids present in the sample based on the quantifying of (a) to the nucleic acid sequencing assay, thereby conducting the nucleic acid sequencing assay. In some cases, the reaction mixture comprises a hybridization buffer. In some cases, the hybridization buffer comprises citrate, sodium chloride, or both. In some cases, the hybridization buffer is HT1 buffer. In some cases, the directly utilizes the template nucleic acids such that the template nucleic acids in the hybridization buffer are not processed to a lower concentration of citrate, sodium chloride, or both in the hybridization buffer prior to the qPCR. In some cases, the citrate, sodium chloride, or both is present in the nucleic acid amplification reaction mixture an amount that would otherwise inhibit quantitative polymerase chain reaction (qPCR) when performed in a nucleic acid amplification reaction mixture containing more than 10 mM potassium chloride. In some cases, the subjecting comprises hybridizing the appropriate amount of the template nucleic acids to one or more probes immobilized on a solid support. In some cases, the method further comprises amplifying the appropriate amount of the template nucleic acids on the solid support thereby generating amplified immobilized nucleic acids. In some cases, the method further comprises a sequencing-by-synthesis reaction on the amplified immobilized nucleic acids.

In yet another aspect, a reaction mixture for nucleic acid amplification is provided, comprising: (a) one or more template nucleic acids; (b) one or more primers, each of which comprises a nucleotide sequence that is complementary to a nucleotide sequence of the one or more template nucleic acids; (c) less than about 10 mM potassium salt; (d) a plurality of nucleotides or analogues thereof; (e) $MgCl_2$; (f) a buffer; and (g) a polymerase enzyme. In some cases, the reaction mixture is substantially free of ammonium salt. In some instances, the reaction mixture comprises sodium citrate. In some instances, the sodium citrate is present in the reaction mixture at a concentration of about 0.15 mM to about 15 mM. In some instances, the reaction mixture comprises sodium chloride. In some cases, the sodium chloride is present in the reaction mixture at a concentration of about 1.5 mM to about 150 mM. In some cases, the potassium salt is potassium chloride. In some cases, the reaction mixture is substantially free of potassium salt. In some cases, the plurality of nucleotides or analogues thereof are present in the reaction mixture at a concentration of about 0.05 mM to about 1 mM. In some cases, the $MgCl_2$ is present in the reaction mixture at a concentration of about 0.5 mM to about 20 mM. In some cases, the polymerase enzyme comprises Taq DNA polymerase. In some cases, the reaction mixture further comprises a detergent at a concentration of less than about 0.5% v/v. In some cases, the reaction mixture further comprises an organic solvent at a concentration of less than about 15% v/v. In some cases, the reaction mixture further comprises glycerol at a concentration of less than about 20% v/v. In some cases, the reaction mixture comprises a pH from about 7.0 to about 9.5. In some cases, the buffer comprises Tris.

In another aspect, a kit containing reagents for amplifying nucleic acids is provided, the kit comprising: (a) a buffer; (b) $MgCl_2$; (c) nucleotides or analogues thereof; (d) optionally, potassium chloride; and (e) instructions for use of the kit for amplifying nucleic acids, wherein reagents (a) through (d) are packaged in one or more separate containers or in a single container, and wherein, when used in a nucleic acid amplification reaction mixture: (i) the $MgCl_2$ is present therein in a concentration from about 0.5 mM to about 20 mM; (ii) the nucleotides or analogues thereof are present therein in a concentration from about 0.05 mM to about 1.0 mM; (iii) the buffer is present therein in a concentration from about 5 mM to about 50 mM; and (iv) the potassium chloride, if present, is present therein in a concentration of less than about 10 mM. In some instances, the buffer comprises Tris. In some instances, the kit further comprises a polymerase enzyme. In some cases, the polymerase enzyme is Taq DNA polymerase. In some cases, the nucleic acid amplification reaction mixture is substantially free of potassium chloride. In some cases, the kit further comprises ammonium salt. In some instances, the ammonium salt is ammonium chloride or ammonium sulfate. In some examples, when used in a nucleic acid amplification reaction mixture, the ammonium salt is present therein in a concentration of about 30 mM or less. In some instances, the kit further comprises a detergent. In some examples, when used in a nucleic acid amplification reaction mixture, the detergent is present therein in a concentration of about 0.5% or less. In some instances, the kit further comprises an organic solvent. In some examples, when used in a nucleic acid amplification reaction mixture, the organic solvent is present therein in a concentration of about 5% or less. In some instances, the kit further comprises glycerol. In some examples, when used in a nucleic acid amplification reaction mixture, the glycerol is present therein in a concentration of about 10% or less. In some instances, the kit further comprises a betaine. In some examples, when used in a nucleic acid amplification reaction mixture, the betaine is present therein in a concentration of about 5 M or less. In some cases, when (a)-(d) are used in a nucleic acid amplification reaction mixture, the nucleic acid amplification reaction mixture has a pH of about 7.0 to about 9.5. In some cases, the instructions describe use of the kit in multiple language.

In another aspect, a method of using a kit as described above is provided, the method comprising: (a) generating a nucleic acid amplification reaction mixture comprising: (i) (a)-(d); and (ii) one or more template nucleic acids; and (b) performing a nucleic acid amplification reaction with the nucleic acid amplification reaction mixture under conditions to yield amplified products of the one or more template nucleic acids.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 (panel B) tabulates amplification reaction components as described in Example 1;

FIG. 8 (panel B) graphically depicts experimental data obtained from nucleic acid amplification as described in Example 4.

DETAILED DESCRIPTION

Figure 1:
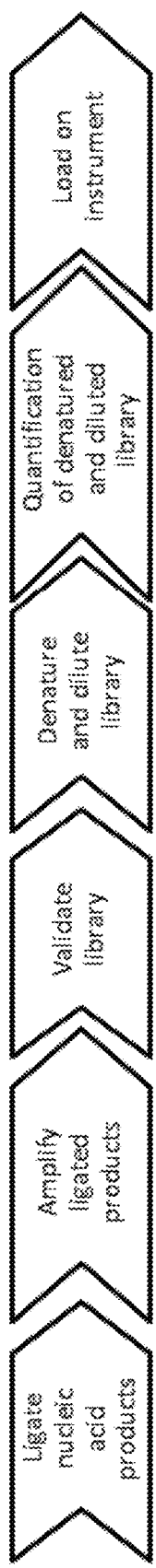
FIG. 1 schematically depicts an example workflow for preparing a sample for nucleic acid sequencing.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an" and "the" include plural references unless the context clearly dictates otherwise. For example, the term "a cell" includes a plurality of cells, including mixtures thereof.

As used herein, the term "about" a number refers to that number plus or minus 10% of that number. The term "about" a range refers to that range minus 10% of its lowest value and plus 10% of its greatest value.

As used herein, the terms "amplifying" and "amplification" are used interchangeably and generally refer to generating one or more copies or "amplified product" of a nucleic acid. The term "DNA amplification" generally refers to generating one or more copies of a DNA molecule or "amplified DNA product".

As used herein, the term "cycle threshold" or "Ct" generally refers to the cycle during thermal cycling of a nucleic acid amplification reaction in which an increase in a detectable signal due to amplified product reaches a statistically significant level above background signal.

As used herein, the terms "denaturing" and "denaturation" are used interchangeably and generally refer to the full or partial unwinding of the helical structure of a double-stranded nucleic acid, and in some cases the unwinding of the secondary structure of a single stranded nucleic acid. Conditions at which denaturation may occur include a "denaturation temperature" that generally refers to a temperature at which denaturation is permitted to occur and a "denaturation duration" that generally refers to an amount of time allotted for denaturation to occur.

As used herein, the term "elongation" generally refers to the incorporation of nucleotides to a nucleic acid in a template directed fashion. Elongation may occur via the aid of an enzyme, such as, for example, a polymerase. Conditions at which elongation may occur include an "elongation temperature" that generally refers to a temperature at which elongation is permitted to occur and an "elongation duration" that generally refers to an amount of time allotted for elongation to occur.

As used herein, the term "nucleic acid" generally refers to a polymeric form of nucleotides of any length, either deoxyribonucleotides (dNTPs) or ribonucleotides (rNTPs), or analogs thereof Nucleic acids may have any three dimensional structure, and may perform any function, known or unknown. Non-limiting examples of nucleic acids include deoxyribonucleic acid (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a nucleic acid detection agent.

As used herein, the term "primer extension reaction" generally refers to the denaturing of a double-stranded nucleic acid, binding of a primer to one or both strands of the denatured nucleic acid, followed by elongation of the primer(s).

As used herein, the term "reaction mixture" or "nucleic acid amplification reaction mixture" are used interchangeably and generally refer to a composition comprising reagents necessary to perform, conduct and complete a nucleic acid amplification reaction (e.g., DNA amplification). Non-limiting examples of such reagents can include: template nucleic acids, primers comprising nucleotide sequence(s) that is/are complementary to nucleotide sequence(s) on a nucleic acid and can effect template-directed nucleic acid amplification, a polymerase, suitable buffers (including zwitterionic buffers), co-factors (e.g., divalent and monovalent cations. metal ions), nucleotides and analogues thereof (e.g., dNTPs), and other enzymes (e.g., uracil-DNA glycosylase (UNG)), etc). In some embodiments, a polymerase is a DNA polymerase. Non-limiting examples of DNA polymerases include Taq polymerase, Tth polymerase, Tli polymerase, Pfu polymerase, VENT® polymerase, DEEPVENT® polymerase, EX-Taq™ polymerase, LA-Taq® polymerase, Expand™ polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum® Taq polymerases, Hi-Fi polymerase, Tbr polymerase, Tfl polymerase, PfuTurbo® polymerase, Pyrobest® polymerase, Pwo polymerase, KOD polymerase, Bst polymerase, Sac polymerase, Klenow fragment, Phusion® High-Fidelity Polymerase, Q5® High-Fidelity Polymerase and variants, modified products and derivatives thereof. In some cases, a polymerase is a hot-start polymerase whose activity can depend on reaction temperature. Moreover, in some embodiments, a reaction mixture comprises one or more nucleic acid detection agents.

Moreover, as is discussed elsewhere herein, a reaction mixture may comprise one or more substances that can inhibit or negatively impact a nucleic acid amplification reaction. Non-limiting examples of inhibitors include citrate, sodium chloride, heme, EDTA, heparin, hemoglobin, lactoferrin, bile salts, bilirubin, calcium chloride, iron(III) chloride, polysaccharides, collagen, humic acid, melanin, eumelanin, myoglobin, proteinases, calcium ions, urea, immunoglobulin G, and indigo dye. In some cases, the inhibitory activity of a given inhibitor may depend on the presence of one or more additional species in the reaction mixture. For example, the inhibitory effects of citrate can depend on the presence of a potassium salt. In the absence of or in the presence of a reduced amount of the one or more additional species, the inhibitor has reduced or even no inhibitory effect. For example, in the absence or presence of a reduced amount of a potassium salt, a citrate inhibitor can lose some of all of its inhibitory activity. In some cases, a reaction may comprise a buffer that comprises one or more inhibitory species. Non-limiting examples of such buffers include HT1 buffer, saline sodium citrate buffer (SSC buffer), and acid citrate dextrose (ACD).

As used herein, a "nucleic acid detection agent" generally refers to a composition that yields a detectable signal, the presence or absence of which can be used to detect the presence of amplified product and/or an intensity of which can be used to quantify an amount of amplified product. The intensity of the detectable signal may be proportional to an amount of amplified product. The use of a nucleic acid detection agent also enables quantitative amplification schemes, including qPCR. Nucleic acid detection agents may be linked with nucleic acids, including amplified products, covalently or non-covalently. Non-limiting examples of non-covalent linkages include ionic interactions, Van der Waals forces, hydrophobic interactions, hydrogen bonding, and combinations thereof. In some embodiments, a nucleic acid detection agent binds to initial reactants and changes in agent level may be used to detect amplified product. In some embodiments, a nucleic acid detection agent is only be detectable (or non-detectable) as nucleic acid amplification progresses.

In some embodiments, an optically-active dye (e.g., a fluorescent dye) is used as a nucleic acid detection agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methyl coumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some embodiments, a nucleic acid detection agent is a sequence-specific oligonucleotide probe that is optically active when hybridized with an amplified product. Due to sequence-specific binding of the probe to the amplified product, use of oligonucleotide probes can increase specificity and sensitivity of detection. A probe may be linked to any of the optically-active nucleic acid detection agent (e.g., dyes) described herein and may also include a quencher capable of blocking the optical activity of an associated dye. Non-limiting examples of probes that may be useful used as nucleic acid detection agent include TaqMan probes, TaqMan Tamara probes, TaqMan MGB probes, or Lion probes.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogues thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the term "subject," generally refers to an entity or a medium that has testable or detectable genetic information. A subject can be a person or individual. A subject can be a vertebrate, such as, for example, a mammal or an avian. Non-limiting examples of mammals include murines, simians, humans, rodents, farm animals, sport animals, and pets (e.g., a dog, a cat, a rodent, a bird, other mammals, a reptile, a fish or other form of marine life, etc.). Other examples of subjects include food, plant, soil, and water. Nucleic acid can be obtained from a subject or other source as a sample, either directly or indirectly. In some cases, the sample may be a biological sample, such as blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. In some cases, a sample may be pre-processed in one or more procedures to extract nucleic acid to-be-analyzed from the sample and/or separate the nucleic acid from other components of the sample. In other cases, the sample may be directly analyzed without further processing. In some cases, the sample may comprise a nucleic acid library, such as a library of nucleic acids that have been generated for compatibility with a nucleic acid sequencing reaction.

Disclosed herein are compositions and methods for performing nucleic acid amplification reactions, including in reaction mixtures that comprise potentially inhibitory species to amplification and/or quantitative analysis. The compositions and methods described herein are suitable for quantifying the amount of nucleic acid molecules present in a sample and/or nucleic acid amplification reaction mixture, including where potentially inhibitory species are present. In some cases, compositions and methods are suitable for analyzing nucleic acids in an assay preparation, including a sequencing assay preparation.

With regard to preparation of a nucleic acid for a sequencing assay and use of the preparation for a sequencing assay, a sample workflow is schematically depicted in FIG. 1. As shown in FIG. 1, a nucleic acid sample is obtained and processed to ligate sequencing adaptors to nucleic acids derived from the sample. The ligated products are then amplified in one or more nucleic acid amplification reactions to generate a sequencing library. The library is then validated and subject to denaturing conditions to denature nucleic acids into single stranded nucleic acids that are suitable for interaction with a given sequencing chemistry completed with a sequencing instrument. The single-stranded nucleic acids are then diluted in a processing buffer (e.g., HT1 buffer) that enables compatibility of the single-stranded nucleic acids with the sequencing chemistry and/or one or more components of the sequencing instrument. The preparation is then subject to a quantitative nucleic acid amplification reaction (e.g., qPCR) to quantify the amount of template in the preparation. In some cases, the preparation is not subject to additional dilution prior to quantifying the template in the preparation. Once the preparation is analyzed, the sample is then, if necessary, further processed with additional diluent and then loaded onto a sequencing instrument for analysis. Compositions and methods can be compatible with any suitable sequencing modality. Non-limiting examples of sequencing modalities include sequencing-by-synthesis methods, including those available from Illumina, Inc. (e.g., GXII, NextSeq, MiSeq, HiSeq, X10), Ion Torrent division of ThermoFisher Scientific (e.g., Ion Proton and Ion PGM) and pyrosequencing methods.

In one aspect, the disclosure provides a method for amplifying one or more template nucleic acids. The method comprises: (a) providing a nucleic acid amplification reaction mixture comprising: (i) the one or more template nucleic acids; (ii) reagents necessary for conducting a nucleic acid amplification reaction; and (iii) citrate and sodium chloride. The method also comprises (b) performing the nucleic acid amplification reaction with the nucleic acid amplification reaction mixture under conditions to yield amplified products of the one or more template nucleic acids.

In another aspect, the disclosure provides a method for amplifying one or more template nucleic acids present in a sample. The method comprises: (a) providing a nucleic acid amplification reaction mixture comprising: (i) the one or more template nucleic acids; (ii) reagents necessary for conducting a nucleic acid amplification reaction; and (iii) less than about 10 millimolar (mM) potassium salt. In some embodiments, the nucleic acid amplification reaction mixture is substantially free of ammonium salt. The method also comprises (b) performing the nucleic acid amplification reaction with the nucleic acid amplification reaction mixture under conditions to yield amplified products of the one or more template nucleic acids.

With respect to the aforementioned aspects, performing nucleic acid amplification can comprise one or more of (i) denaturing the one or more template nucleic acids to generate one or more denatured template nucleic acids; (ii) annealing a primer to the one or more denatured template nucleic acids; (iii) extending the primer to generate one or more extended nucleic acids; and (iv) repeating (i)-(iii) using one or more extended nucleic acids as templates to generate the amplified products. In some of the aforementioned aspects, performing nucleic acid amplification can comprise performing polymerase chain reaction (PCR), such as, for example, qPCR or performing another type of quantitative nucleic acid amplification reaction. In some cases, quantitative nucleic acid amplification, such as qPCR, is real time in that the course of the reaction is monitored as it proceeds. In other cases, quantitative nucleic acid amplification includes an end-point measurement, after the reaction concludes. Furthermore, with respect to the aforementioned aspects, a method can further comprise determining a concentration of the one or more template nucleic acids present in the sample.

In another aspect, the disclosure provides a method for conducting a nucleic acid sequencing assay. (a) quantifying an amount of template nucleic acids in a sample to be sequenced by performing a quantitative polymerase chain reaction (qPCR) in a nucleic acid amplification reaction mixture, wherein the qPCR directly utilizes the template nucleic acids present in the sample, wherein the sample contains citrate, sodium chloride, or both; (b) subjecting an appropriate amount of the template nucleic acids present in the sample based on the quantifying of (a) to the nucleic acid sequencing assay, thereby conducting the nucleic acid sequencing assay.

In another aspect, the disclosure provides a method for conducting a nucleic acid sequencing assay. The method comprises (a) quantifying an amount of template nucleic acids in a sample to be sequenced by performing a quantitative polymerase chain reaction (qPCR) in a nucleic acid amplification reaction mixture. In some embodiments, the nucleic acid amplification reaction mixture comprises less than about 10 mM potassium salt and the nucleic acid amplification reaction mixture is substantially free of ammonium salt. The method also comprises (b) subjecting an appropriate amount of the template nucleic acids present in the sample based on the quantifying of (a) to the nucleic acid sequencing assay, thereby conducting the nucleic acid sequencing assay.

In some of the aforementioned aspects, subjecting template nucleic acids present in the sample comprises one more of (i) hybridizing the appropriate amount of the template nucleic acids to one or more probes immobilized on a solid support; (ii) amplifying the appropriate amount of the template nucleic acids on the solid support thereby generating amplified immobilized nucleic acids; and (iii) performing a sequencing-by-synthesis reaction on the amplified immobilized nucleic acids. In some embodiments, a method includes each of (i)-(iii), consistent with Illumina sequencing technology. Briefly, each the one or more probes may be immobilization oligonucleotides that are immobilized to the surface of a flow cell of a sequencer (e.g., GXII, NextSeq, MiSeq, HiSeq, X10) having a plurality of independently addressable regions arranged in an array each comprising one or more of the probes. The template nucleic acids can hybridize with probes at each region and be subjected to clonal amplification, such that a colony of nucleic acids having at least a portion of the same sequence are generated. The colonies can then be subject to a sequencing-by-synthesis reaction using sequencing primers and labelled nucleotides that are detected upon their incorporation into the templates in primer extension reactions.

In another aspect, the disclosure provides a reaction mixture for nucleic acid amplification. The reaction mixture comprises one or more of (a) one or more template nucleic acids; (b) one or more primers, each of which comprises a nucleotide sequence that is complementary to a nucleotide sequence of the one or more template nucleic acids; (c) less than about 10 millimolar (mM) potassium salt; (d) a plurality of nucleotides or analogues thereof; (e) $MgCl_2$; (f) a buffer; and (g) a polymerase enzyme.

In various aspects, a reaction mixture comprises or can comprise citrate. Citrate can be present in the reaction mixture in its free form or may be present as part of a metal-citrate salt (e.g., sodium citrate). Moreover, the citrate may be present in the reaction mixture as a result of its inclusion in the sample as a part of sample processing with a buffer comprising citrate (e.g., HT1 buffer). As is discussed elsewhere herein, citrate can inhibit nucleic acid amplification, including in the presence of a potassium salt, such as potassium chloride. The concentration of citrate in a reaction mixture can vary depending upon the particular reaction mixture utilized.

For example, citrate may be present in a reaction mixture at a concentration from about 0.3 mM to about 1 mM, from about 3 mM to about 300 mM, from about 1 mM to about 100 mM, from about 0.5 mM to about 50 mM, from about 0.25 mM to about 25 mM or from about 0.15 mM to about 15 mM. In some embodiments, citrate is present in a reaction mixture at a concentration of at least about 0.01 mM, at least about 0.1 mM, at least about 0.5 mM, at least about 1 mM, at least about 3 mM, at least about 5 mM, at least about 10 mM, at least about 15 mM, at least about 20 mM, at least about 25 mM, at least about 50 mM, at least about 100 mM, at least about 150 mM, at least about 200 mM, at least about 300 mM, at least about 400 mM, at least about 500 mM, at least about 750 mM, at least about 1 M or higher. Moreover, in some embodiments, citrate is present in an amount that would otherwise inhibit nucleic acid amplification (e.g., qPCR) when performed in the reaction mixture and the reaction mixture, such as when the reaction mixture contains more than or equal to about 0.01 mM, more than or equal to about 0.05 mM, more than or equal to about 0.1 mM, more than or equal to about 0.5 mM, more than or equal to about 1 mM, more than or equal to about 5 mM, more than or equal to about 10 mM, more than or equal to about 25 mM, more than or equal to about 50 mM, more than or about 100 mM or more. Moreover, in some embodiments, a sample provided to a reaction mixture comprises citrate and is directly introduced to the nucleic acid amplification reaction mixture without prior processing to a lower concentration of citrate.

In various aspects, a reaction mixture comprises or can comprise a sodium salt (e.g., sodium chloride). Sodium salt may be present in the reaction mixture as a result of its inclusion in the sample as a part of sample processing with a buffer comprising sodium salt. The concentration of sodium salt in a reaction mixture can vary depending upon the particular reaction mixture utilized. For example, sodium salt may be present in a reaction mixture at a concentration from about 0.1 mM to about 1 M, from about 30 mM to about 3 M, from about 3 mM to about 300 mM, from about 1.5 mM to about 150 mM, from about 0.15 mM to about 25 mM or from about 0.1 mM to about 75 mM. In some embodiments, sodium salt is present in a reaction mixture at a concentration of at least about at least about 0.1 mM, at least about 0.5 mM, at least about 1 mM, at least about 5 mM, at least about 10 mM, at least about 50 mM, at least about 100 mM, at least about 250 mM, at least about 500 mM, at least about 750 mM, at least about 1 M, at least about 3 M, at least about 5 M, at least about 10 M or higher. Moreover, in some embodiments, sodium salt is present in an amount that would otherwise inhibit nucleic acid amplification (e.g., qPCR) when performed in the reaction mixture, such as when the reaction mixture contains more than or equal to about 0.01 mM, more than or equal to about 0.05 mM, more than or equal to about 0.1 mM, more than or equal to about 0.5 mM, more than or equal to about 1 mM, more than or equal to about 5 mM, more than or equal to about 10 mM, more than or equal to about 25 mM, more than or equal to about 50 mM, more than or equal to about 100 mM or more. Moreover, in some embodiments, a sample provided to a reaction mixture comprises sodium salt and is directly introduced to the nucleic acid amplification reaction mixture without prior processing to a lower concentration of sodium salt.

In various aspects, a reaction mixture comprises or can comprise a potassium salt (e.g., potassium chloride). The amount of potassium salt in the reaction mixture may be limited in order to limit the activity of the potassium salt to effect activity of one or more inhibitory species in the reaction mixture. For example, the concentration of potassium salt in the reaction mixture may be less than or equal to about 100 mM, less than or equal to about 75 mm, less than or equal to about 50 mM, less than or equal to about 25 mM, less than or equal to about 10 mM, less than or equal to about 9 mM, less than or equal to about 8 mM, less than or equal to about 7 mM, less than or equal to about 6 mM, less than or equal to about 5 mM, less than or equal to about 4 mM, less than or equal to about 3 mM, less than or equal to about 2 mM, less than or equal to about 1 mM, less than or equal to about 0.5 mM, less than or equal to about 0.1 mM, less than or equal to about 0.01 mM or less. In some embodiments, the reaction mixture is substantially free of potassium salt. In some embodiments, the reaction mixture comprises no potassium salt.

In various aspects, a reaction mixture comprises or can comprise an ammonium salt (e.g., ammonium sulfate, ammonium chloride). The amount of ammonium salt in the reaction mixture may be limited. For example, the concentration of ammonium salt in the reaction mixture may be less than or equal to about 100 mM, less than or equal to about 75 mm, less than or equal to about 50 mM, less than or equal to about 30 mM, less than or equal to about 20 mM, less than or equal to about 10 mM, less than or equal to about 9 mM, less than or equal to about 8 mM, less than or equal to about 7 mM, less than or equal to about 6 mM, less than or equal to about 5 mM, less than or equal to about 4 mM, less than or equal to about 3 mM, less than or equal to about 2 mM, less than or equal to about 1 mM, less than or equal to about 0.5 mM, less than or equal to about 0.1 mM, less than or equal to about 0.01 mM or less. In some embodiments, the reaction mixture is substantially free of ammonium salt. In some embodiments, the reaction mixture comprises no ammonium salt.

In various aspects, a reaction mixture comprises or can comprise a magnesium salt (e.g., magnesium chloride). A magnesium salt can function as a co-factor in effecting nucleic acid amplification. Magnesium salt may be present in the reaction mixture as a result of its inclusion in the sample as a part of sample processing with a buffer comprising magnesium salt. The concentration of magnesium salt in a reaction mixture can vary depending upon the particular reaction mixture utilized. For example, magnesium salt may be present in a reaction mixture at a concentration from about 0.1 mM to about 500 mM, from about 0.1 mM to about 100 mM, from about 0.5 mM to about 50 mM, from about 0.5 mM to about 20 mM, from about 0.5 mM to about 10 mM or from about 1 mM to about 5 mM. In some embodiments, magnesium salt is present in a reaction mixture at a concentration of less than or equal to about 200 mM, less than or equal to about 100 mM, less than or equal to about 75 mM, less than or equal to about 50 mM, less than or equal to about 40 mM, less than or equal to about 30 mM, less than or equal to about 20 mM, less than or equal to about 10 mM, less than or equal to about 5 mM, less than or equal to about 1 mM, less than or equal to about 0.5 mM, less than or equal to about 0.1 mM or less. Moreover, in some embodiments, a sample provided to a reaction mixture comprises magnesium salt and is directly introduced to the nucleic acid amplification reaction mixture without prior processing to a lower concentration of magnesium salt.

In various aspects, a reaction mixture comprises or can comprise a detergent. Without wishing to be bound by theory, a detergent may function as, for example, an enzyme stabilizer and/or may prevent the adsorption of reagent components to the PCR tube. Non-limiting examples of a detergent include Tween-20, Tween-40, Tween-60, Tween-80, Triton X-100 and NP-40. A detergent may be present in the reaction mixture as a result of its inclusion in the sample as a part of sample processing with a buffer comprising detergent. The concentration of detergent in a reaction mixture can vary depending upon the particular reaction mixture utilized. For example, detergent may be present in a reaction mixture at a concentration from less than or equal to about 5% volume per volume (v/v), less than or equal to about 4% v/v, less than or equal to about 3% v/v, less than or equal to about 2% v/v, less than or equal to about 1% v/v, less than or equal to about 0.5% v/v, less than or equal to about 0.1% v/v, less than 0.05% v/v, less than 0.01% v/v or less. Moreover, in some embodiments, a sample provided to a reaction mixture comprises detergent and is directly introduced to the nucleic acid amplification reaction mixture without prior processing to a lower concentration of detergent.

In various aspects, a reaction mixture comprises or can comprise one or more organic solvents. Without wishing to be bound by theory, an organic solvent may function to destabilize nucleic acid secondary structures and decrease the temperature at which strand separation occurs during a nucleic acid amplification reaction. Non-limiting examples of suitable organic solvents include dimethylsulfoxide (DMSO), ethylene glycol, and propylene glycol. An organic solvent may be present in the reaction mixture as a result of its inclusion in the sample as a part of sample processing with a buffer comprising organic solvent. The concentration of organic solvent in a reaction mixture can vary depending upon the particular reaction mixture utilized. For example, organic solvent may be present in a reaction mixture at a concentration from less than or equal to about 30% v/v, less than or equal to about 20% v/v, less than or equal to about 15% v/v, less than or equal to about 10% v/v, less than or equal to about 8% v/v, less than or equal to about 6% v/v, less than or equal to about 4% v/v, less than or equal to about 2% v/v, less than or equal to about 1% v/v or less. Moreover, in some embodiments, a sample provided to a reaction mixture comprises organic solvent and is directly introduced to the nucleic acid amplification reaction mixture without prior processing to a lower concentration of organic solvent.

In various aspects, a reaction mixture comprises or can comprise glycerol. Without wishing to be bound by theory, glycerol may function as an enzyme stabilizer. Glycerol may be present in the reaction mixture as a result of its inclusion in the sample as a part of sample processing with a buffer comprising glycerol. The concentration of glycerol in a reaction mixture can vary depending upon the particular reaction mixture utilized. For example, glycerol may be present in a reaction mixture at a concentration from less than or equal to about 30% v/v, less than or equal to about 20% v/v, less than or equal to about 15% v/v, less than or equal to about 10% v/v, less than or equal to about 8% v/v, less than or equal to about 6% v/v, less than or equal to about 4% v/v, less than or equal to about 2% v/v, less than or equal to about 1% v/v or less. Moreover, in some embodiments, a sample provided to a reaction mixture comprises glycerol and is directly introduced to the nucleic acid amplification reaction mixture without prior processing to a lower concentration of glycerol.

In various aspects, a reaction mixture comprises or can comprise a betaine. Without wishing to be bound by theory, a betaine may function to destabilize nucleic acid secondary structures. Non-limiting examples of a betaine include N,N,N-trimethylglycine and betaine monohydrate. A betaine may be present in the reaction mixture as a result of its inclusion in the sample as a part of sample processing with a buffer comprising a betaine. The concentration of a betaine in a reaction mixture can vary depending upon the particular reaction mixture utilized. For example, a betaine may be present in a reaction mixture at a concentration from about 100 mM to about 20 molar (M), from about 100 mM to about 10 M, from about 500 mM to about 10 M, from about 500 mM to about 5 M, from about 1 M to about 5 M or from about 3 M to about 5 M. In some embodiments, a betaine is present in a reaction mixture at a concentration of less than or equal to about 20 M, less than or equal to about 15 M, less than or equal to about 10 M, less than or equal to about 5M, less than or equal to about 3 M, less than or equal to about 2 M, less than or equal to about 1M, less than or equal to about 500 mM, less than or equal to about 250 mM, less than or equal to about 100 mM, less than or equal to about 50 mM, less than or equal to about 10 mM or less. Moreover, in some embodiments, a sample provided to a reaction mixture comprises a betaine and is directly introduced to the nucleic acid amplification reaction mixture without prior processing to a lower concentration of the betaine.

In various aspects, a reaction mixture generally comprises nucleotides or analogues thereof. Nucleotides (or their analogues) are incorporated in template directed fashion during a nucleic acid amplification reaction. The concentration of nucleotides or analogues thereof in a reaction mixture can vary depending upon the particular reaction mixture utilized. For example, nucleotides or analogues thereof may be present in a reaction mixture at a concentration from about 0.01 mM to about 10 mM, from about 0.01 mM to about 5 mM, from about 0.05 mM to about 3 mM, from about 0.05 mM to about 1 mM, from about 0.05 mM to about 0.5 mM or from about 1 mM to about 0.5 mM.

In various aspects, a nucleic acid amplification reaction mixture comprises or can comprise one or more buffers. A buffer can include one or more species that aid in maintaining the reaction conditions (e.g., pH, ionic strength, etc.) in the reaction mixture. Non-limiting examples of such buffers include Tris-HCl, tricine, 2-[4-(2-hydroxyethyl)piperazin-1-yl]ethanesulfonic acid (HEPES), and 3-morpholinopropane-1-sulfonic acid (MOPS). A buffer can be provided to a reaction mixture due to its presence as a part of the nucleic acid sample provided to the reaction mixture. As described elsewhere herein, such a buffer can aid in permitting sample capability with a given downstream assay. For example, in the context of a sequencing assay, the buffer may be a hybridization buffer (e.g., HT1) that aids hybridization of nucleic acids in the sample to components of a sequencing instrument, such as immobilization primers on a sequencing array.

A reaction mixture can have any suitable pH that permits nucleic acid amplification to occur in the reaction mixture. For example, the reaction mixture may have a pH from about 6.0 to about 10.0, from about 6.5 to about 9.5, from about 7.0 to about 9.5, from about 7.0 to about 9.0, from about 7.0 to about 8.5 or from about 7.5 to about 8.5. As described elsewhere herein pH can be modulated by the inclusion of one or more buffer species in the reaction mixture.

Examples of nucleic acid amplification reaction mixtures comprising various components described herein are tabulated below in Tables 1-5:

TABLE 1

Example nucleic acid amplification reaction mixture A

| Reagent | Concentration |
| --- | --- |
| Tris-HCl pH 8.3 | 15-20 mM |
| Magnesium Chloride (MgCl$_2$) | 10-20 mM |
| dNTPs | 0.3-0.5 mM |
| Tween-20 | 0.1-0.5% |
| DMSO | 5-10% |
| EvaGreen Dye | 1-3X |
| Sodium Azide (NaN$_3$) | 0.09-0.20% |
| Ammonium sulfate, (NH$_4$)$_2$SO$_4$ | 10-15 mM |
| ROX Dye | 0.05-1 µM |
| Glycerol | 1-5% |
| Taq Polymerase (optionally, hot-start Taq) | 0.2-0.5 units (U)/µL |
| Sodium Citrate | 1-11.25 mM |
| Sodium Chloride (NaCl) | 10-112.5 mM |
| Potassium Chloride (KCl) | <10 mM |

TABLE 2

Example nucleic acid amplification reaction mixture B

| Reagent | Concentration |
| --- | --- |
| Tris-HCl pH 8.3 | 10-15 mM |
| Magnesium Chloride (MgCl$_2$) | 1-6 mM |
| dNTPs | 0.1-0.5 mM |
| Tween-20 | 0.05-0.15% |
| DMSO | 0.5-3.0% |
| EvaGreen Dye | 0.5-2X |
| Sodium Azide (NaN$_3$) | 0.045-0.09% |
| Ammonium sulfate, (NH$_4$)$_2$SO$_4$ | 0 mM |
| ROX Dye | 0.05-0.5 µM |
| Glycerol | 5-15% |
| Taq Polymerase (optionally, hot-start Taq) | 0.05-0.9 U/µL |
| Sodium Citrate | 0-13.13 mM |
| Sodium Chloride (NaCl) | 0-131.25 mM |
| Potassium Chloride (KCl) | 0 mM |

TABLE 3

Example nucleic acid amplification reaction mixture C

| Reagent | Concentration |
| --- | --- |
| Tris-HCl pH 8.3 | 10-20 mM |
| Magnesium Chloride (MgCl$_2$) | 15-20 mM |
| dNTPs | 0.5-0.9 mM |
| Tween-20 | 0.1-0.5% |
| DMSO | 7-15% |
| EvaGreen Dye | 1-3 x |
| Sodium Azide (NaN$_3$) | 0.09-0.20% |
| Ammonium sulfate, (NH$_4$)$_2$SO$_4$ | 0 mM |
| ROX Dye | 0.05-1 µM |
| Glycerol | 1-5% |
| Taq Polymerase (optionally, hot-start Taq) | 0.2-0.5 U/µL |
| Sodium Citrate | 0.1-7.5 mM |
| Sodium Chloride (NaCl) | 1-75 mM |
| Potassium Chloride (KCl) | 0 mM |

TABLE 4

Example nucleic acid amplification reaction mixture D

| Reagent | Concentration |
| --- | --- |
| Tris-HCl pH 8.3 | 1-10 mM |
| Magnesium Chloride (MgCl$_2$) | 1-10 mM |
| dNTPs | 0.05-0.2 mM |
| Tween-20 | 0.01-0.07% |
| DMSO | 0.5-3.0% |
| EvaGreen Dye | 0.5-2 x |
| Sodium Azide (NaN$_3$) | 0.045-0.09% |
| Ammonium sulfate, (NH$_4$)$_2$SO$_4$ | <30 mM |
| ROX Dye | 0.05-0.5 µM |
| Glycerol | 7-20% |
| Taq Polymerase (optionally, hot-start Taq) | 0.05-0.9 U/µL |
| Sodium Citrate | 0-13.13 mM |
| Sodium Chloride (NaCl) | 0-131.25 mM |
| Potassium Chloride (KCl) | <10 mM |

TABLE 5

Example nucleic acid amplification reaction mixture E

| Reagent | Concentration |
| --- | --- |
| Tris-HCl pH 8.3 | 8-20 mM |
| Magnesium Chloride (MgCl$_2$) | 4-10 mM |
| dNTPs | 0.1-0.5 mM |
| Tween-20 | 0.01-0.07% |
| DMSO | 2.0-5.0% |
| EvaGreen Dye | 0.5-1 x |
| Sodium Azide (NaN$_3$) | 0.045-0.09% |
| Ammonium sulfate, (NH$_4$)$_2$SO$_4$ | 10-30 mM |
| ROX Dye | 0.05-0.2 µM |
| Glycerol | 2-10% |
| Taq Polymerase (optionally, hot-start Taq) | 0.1-0.5 units (U)/µL |
| Sodium Citrate | 0-13.13 mM |
| Sodium Chloride (NaCl) | 0-131.25 mM |
| Potassium Chloride (KCl) | <10 mM |

In another aspect, the disclosure provides a kit containing reagents for amplifying nucleic acids. The kit comprises (a) a buffer (e.g., a Tris buffer); (b) MgCl$_2$; (c) nucleotides or analogues thereof; (d) optionally, potassium chloride; and (e) instructions for use of the kit for amplifying nucleic acids. In some embodiments, reagents (a) through (d) are packaged in one or more separate containers or in a single container and when used in a nucleic acid amplification reaction mixture: (i) the MgCl$_2$ is present therein in a concentration from about 0.5 mM to about 20 mM; (ii) the nucleotides or analogues thereof are present therein in a concentration from about 0.05 mM to about 1.0 mM; (iii) the buffer is present therein in a concentration from about 5 mM to about 50 mM; and (iv) the potassium chloride, if present, is present therein in a concentration of less than about 10 mM. In some embodiments, each component of (i)-(iv) can be present in the nucleic acid amplification reaction mixture over another range of concentrations, including other example concentration ranges described for each component in (i)-(iv) described elsewhere herein. In some embodiments, the instructions describe use of the kit in multiple languages.

In some embodiments, the kit further comprises one or more of a polymerase, an ammonium salt (e.g., ammonium chloride or ammonium sulfate), a detergent, an organic solvent, glycerol and a betaine. Any of these components can be packaged in separate containers or combined with one or more kit components in a given container. Moreover, when used in the nucleic acid amplification reaction mixture, each component can be present therein in concentrations or amounts described with respect to each component as part of a reaction mixture described elsewhere herein. Moreover, when kit components are used in a reaction mixture, the reaction mixture can have any suitable pH, including within an example reaction mixture pH range described elsewhere herein. Furthermore, the nucleic acid amplification reaction mixture may be substantially free of potassium chloride and/or an ammonium salt.

In another aspect, the disclosure provides a method of using a kit described herein. In some embodiments, the method comprises (a) generating a nucleic acid amplification reaction mixture comprising: (i) the (a)-(d); and (ii) one or more template nucleic acids; and (b) performing a nucleic acid amplification reaction with the nucleic acid amplification reaction mixture under conditions to yield amplified products of the one or more template nucleic acids.

In various aspects, methods described herein can include performing a nucleic acid amplification reaction. The nucleic acid amplification reaction can be any suitable nucleic acid amplification reaction, including both thermal-cycling and isothermal approaches. Non-limiting examples of types of nucleic acid amplification reactions include primer extension, PCR, ligase chain reaction, variants of PCR (e.g., qPCR, including real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), helicase-dependent amplification, asymmetric amplification, rolling circle amplification, emulsion nucleic acid amplification, bead-emulsion nucleic acid amplification, multiple displacement amplification (MDA) and ligase chain reaction (LCR). In some cases, nucleic acid amplification is linear. In some cases, nucleic acid amplification is exponential.

Where a given nucleic acid amplification reaction is dependent on thermal cycling, a nucleic acid amplification reaction mixture can be provided to a thermal cycler that cycles the temperature of the nucleic acid reaction mixture between a denaturation and elongation temperature, for denaturation and elongation durations. A denaturation temperature and duration may vary depending upon the particular nucleic acid amplification reaction mixture used and/or the particular nucleic acid amplification reaction executed. For example, a denaturation temperature may be from about 80° C. to about 110° C. and denaturation duration may be from about 0.5 seconds to about 300 seconds. Similarly, an elongation temperature may vary depending upon, for example, the particular nucleic acid amplification reaction mixture used and/or the particular nucleic acid amplification reaction executed. For example, an elongation temperature may be from about 30° C. to about 80° C. and elongation duration may be from about 0.5 seconds to about 300 seconds.

Furthermore, where an amplification reaction mixture comprises a nucleic acid detection agent, the nucleic acid amplification reaction performed can be quantitatively monitored (e.g., via qPCR), including in real time. Where real time monitoring is employed, monitoring may be achieved with the aid of a real time nucleic acid amplification instrument. Non-limiting examples of such instruments include real-time PCR thermocycler, ABI PRISM® 7000 Sequence Detection System, ABI PRISM® 7700 Sequence Detection System, Applied Biosystems 7300 Real-Time PCR System, Applied Biosystems 7500 Real-Time PCR System, Applied Biosystems 7900 HT Fast Real-Time PCR System (all from Applied Biosystems); LightCycler™ System (Roche Diagnostics GmbH); Mx3000P™ Real-Time PCR System, Mx3005P™ Real-Time PCR System, and Mx4000® Multiplex Quantitative PCR System (Stratagene, La Jolla, Calif.); and Smart Cycler System (Cepheid, distributed by Fisher Scientific). In some embodiments, an amplification module may comprise another automated instrument such as, for example, a COBAS® AmpliPrep/COBAS® TaqMan® system (Roche Molecular Systems), a TIGRIS DTS system (Hologic Gen-Probe, San Diego, Calif.), a PANTHER system (Hologic Gen-Probe, San Diego, Calif.), a BD MAX™ system (Becton Dickinson), a GeneXpert System (Cepheid), a Filmarray® (BioFire Diagnostics) system, an iCubate system, an IDBox system (Luminex), an EncompasslvlDx™ (Rheonix) system, a Liat™ Analyzer (IQuum) system, a Biocartis' Molecular Diagnostic Platform system, an Enigma® ML system (Enigma Diagnostics), a T2Dx® system (T2 Biosystems), a Verigene® system (NanoSphere), a Great Basin's Diagnostic System, a Unyvero™ System (Curetis), a PanNAT system (Micronics), or a Spartan™ RX system (Spartan Bioscience).

In various aspects, methods for including the performing of nucleic acid amplification can yield amplified products that are detected. Where thermal cycling is used thermal cycling can include any suitable number of cycles, (e.g., less than or equal to about 100 cycles, less than or equal to about 90 cycles, less than or equal to about 80 cycles, less than or equal to about 70 cycles, less than or equal to about 60 cycles, less than or equal to about 50 cycles, less than or equal to about 40 cycles, less than or equal to about 30 cycles, less than or equal to about 20 cycles, less than or equal to about 10 cycles, less than or equal to about 5 cycles or less cycles; or greater than or equal to about 5 cycles, greater than or equal to about 10 cycles, greater than or equal to about 20 cycles, greater than or equal to about 30 cycles, greater than or equal to about 40 cycles, greater than or equal to about 50 cycles, greater than or equal to about 60 cycles, greater than or equal to about 70 cycles, greater than or equal to about 80 cycles, greater than or equal to about 90 cycles, greater than or equal to about 100 cycles, or more cycles). The number of cycles (e.g., $C_t$ value) suitable for detection of amplified products, though, can require a minimum number of cycles. However, lower $C_t$ values can improve efficiency and/or reduce the chance for errors. In various aspects, methods that include performing nucleic acid amplification described herein can generate detectable amplified products with lower $C_t$ values. For example, in some embodiments, amplified product may detected at a cycle threshold of less than or equal to about 100 cycles, less than or equal to about 75 cycles, less than or equal to about 70 cycles, less than or equal to about 65 cycles, less than or equal to about 60 cycles, less than or equal to about 55 cycles, less than or equal to about 50 cycles, less than or equal to about 40 cycles, less than or equal to about 35 cycles, less than or equal to about 30 cycles, less than or equal to about 25 cycles, less than or equal to about 20 cycles, less than or equal to about 15 cycles, less than or equal to about 10 cycles, less than or equal to about 5 cycles or less.

Lower cycle threshold values can give rise to lower times for detecting amplified products. Accordingly, methods described herein can permit reduced times to detect amplified products. For example, a method described herein that includes performing nucleic acid amplification may yield a detectable amplified products in less than or equal to about 120 minutes, less than or equal to about 100 minutes, less than or equal to about 60 minutes, less than or equal to about 50 minutes, less than or equal to about 45 minutes, less than or equal to about 40 minutes, less or equal to about 35 minutes, less than or equal to about 30, less than or equal to about 25 minutes, less than or equal to about 20 minutes, less than or equal to about 15 minutes, less than or equal to about 10 minutes, less than or equal to about 5 minutes, less than or equal to about 1 minute or less.

Figure 9:
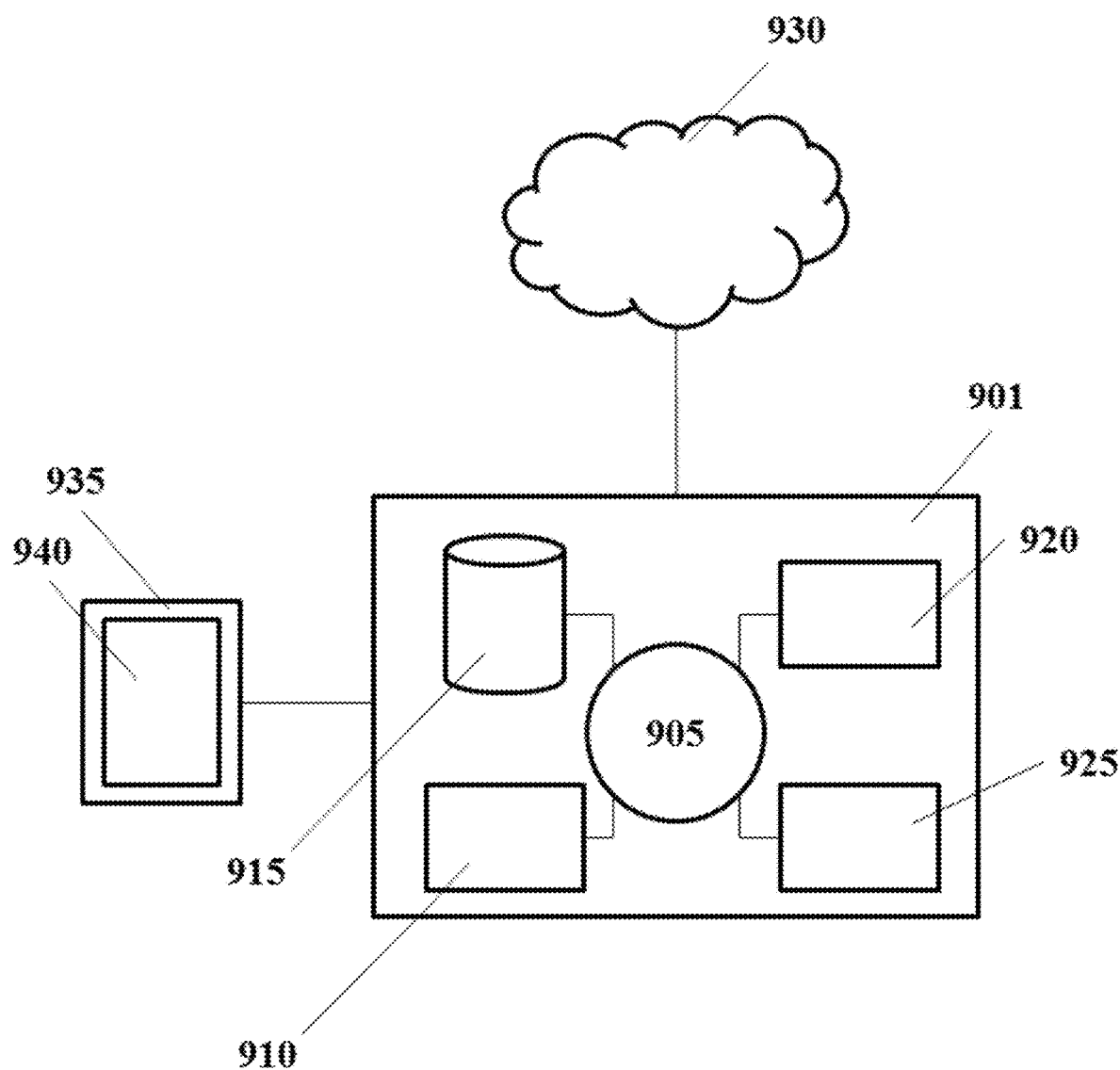
FIG. 9 schematically depicts an example computer control system described herein.

The present disclosure provides computer control systems that are programmed to implement methods of the disclosure. FIG. 9 shows a computer system 901 that is programmed or otherwise configured to effect nucleic acid amplification. The computer system 901 can regulate various aspects of nucleic acid amplification reaction conditions, dispensing or collection of reagents or a nucleic acid amplification reaction mixture acquisition of signals from a nucleic acid amplification reaction mixture, data processing and output, etc. The computer system 901 can be an electronic device of a user or a computer system that is remotely located with respect to the electronic device. The electronic device can be a mobile electronic device. In some cases, the computer system is a component of or is operatively coupled to a thermal cycler and/or quantitative nucleic acid amplification instrument, such as a real-time nucleic acid amplification instrument.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, visual representations of nucleic acid amplification progress, results of a nucleic acid amplification reaction (e.g., including quantitative results), results of data processing, a report summarizing the progress of a nucleic acid amplification reaction and/or any analysis of such a nucleic acid amplification reaction. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, manipulate or generate signals for manipulating fluid handling, modulate thermal cycler operation, etc., process raw data detected from a nucleic acid amplification reaction mixture, etc.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Inhibition of Nucleic Acid Amplification

In a first set of experiments, various amplification reaction mixture preparations were evaluated to determine the feasibility of amplifying a plasmid comprising an insert from the Glyceraldehyde 3-phosphate dehydrogenase (GADPH) gene in each mixture. A total of six mixtures were evaluated, with each reaction mixture subjected to thermal cycling (e.g., 10 min. at 95° C., followed by 40 cycles of 95° C. for 30 seconds and 60° C. for 60 seconds) in a quantitative nucleic acid amplification reaction (e.g., quantitative polymerase chain reaction (qPCR)) and optically monitored. Three of the six mixtures included an aliquot of plasmid in differing amounts (60 picograms (pg), 6 pg and 0.6 pg in 1 µL Tris-EDTA (TE) buffer), 10 µL of SYBR Master Mix comprising multiple reagents necessary for nucleic acid amplification (e.g., a polymerase, dNTPs, etc.), 1 µL of a 5 µM primer mix and PCR grade water to a final volume of 20 µl. The remaining three of six mixtures were identical except for the addition of 1 µL HT1 buffer. The SYBR MasterMix included a SYBR dye and potassium salt (e.g., potassium chloride). The results of each amplification experiment are graphically depicted in FIG. 2.

Figure 2:
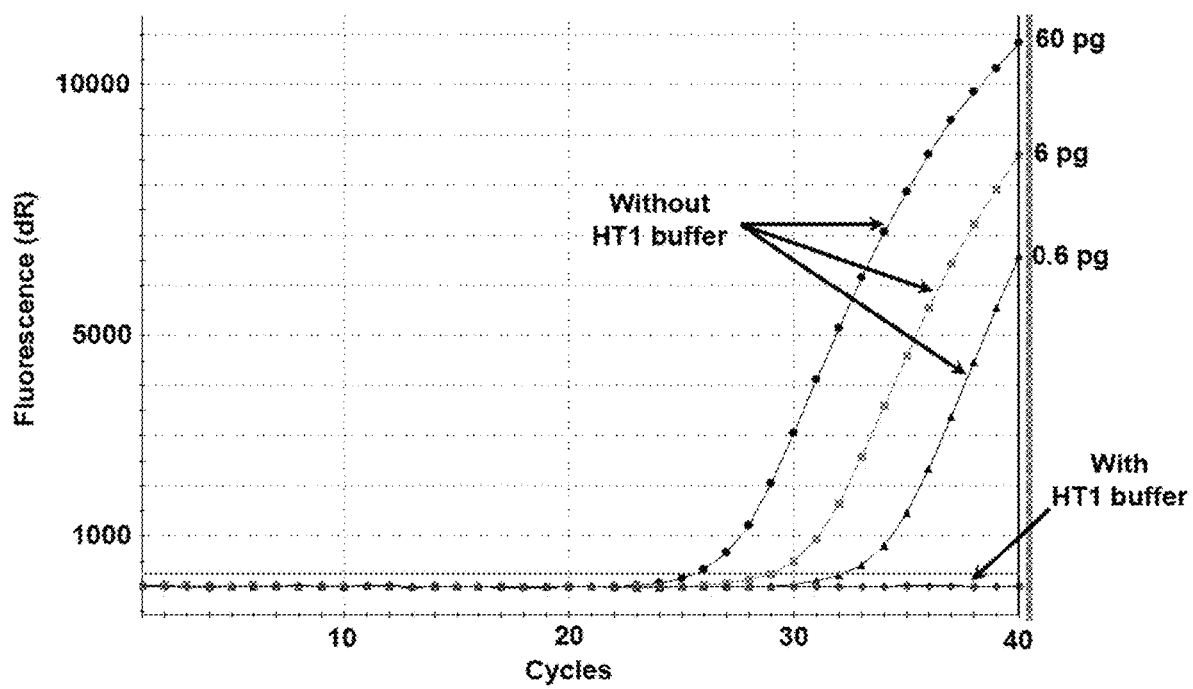
FIG. 2 graphically depicts experimental data obtained from nucleic acid amplification as described in Example 1.

As shown in FIG. 2, each of the three reaction mixtures not comprising HT1 buffer produced detectable amplicons at increasing $C_t$ values (60 µg→$C_t$=25.53, 6 µg→$C_t$=28.93 and 0.6 µg→$C_t$=32.12). However, the three reaction mixtures comprising HT1 buffer did not yield detectable amplicons. Accordingly, data shown in FIG. 2 confirm the inhibitory nature of HT1 in nucleic acid amplification.

In a second set of experiments, two reaction mixture preparations were evaluated to determine the feasibility of amplifying a plasmid comprising an insert from the GADPH gene in each mixture. Each reaction mixture was subjected to thermal cycling (e.g., 10 min. at 95° C., followed by 40 cycles of 95° C. for 30 seconds and 60° C. for 60 seconds) in a quantitative nucleic acid amplification reaction (e.g., qPCR) and optically monitored. One of the reaction mixtures included a 60 µg aliquot of plasmid 1 µL TE buffer, 10 µL of SYBR Master Mix comprising multiple reagents necessary for nucleic acid amplification (e.g., a polymerase, dNTPs, etc.), 1 µL of a 5 µM primer mix and 8 µL of PCR grade water. The SYBR MasterMix included a SYBR dye and potassium salt (e.g., potassium chloride). The second reaction mixture was identical to the first but also included 1 µL of HT1 buffer. The results of each amplification experiment are graphically depicted in FIG. 3.

Figure 3:
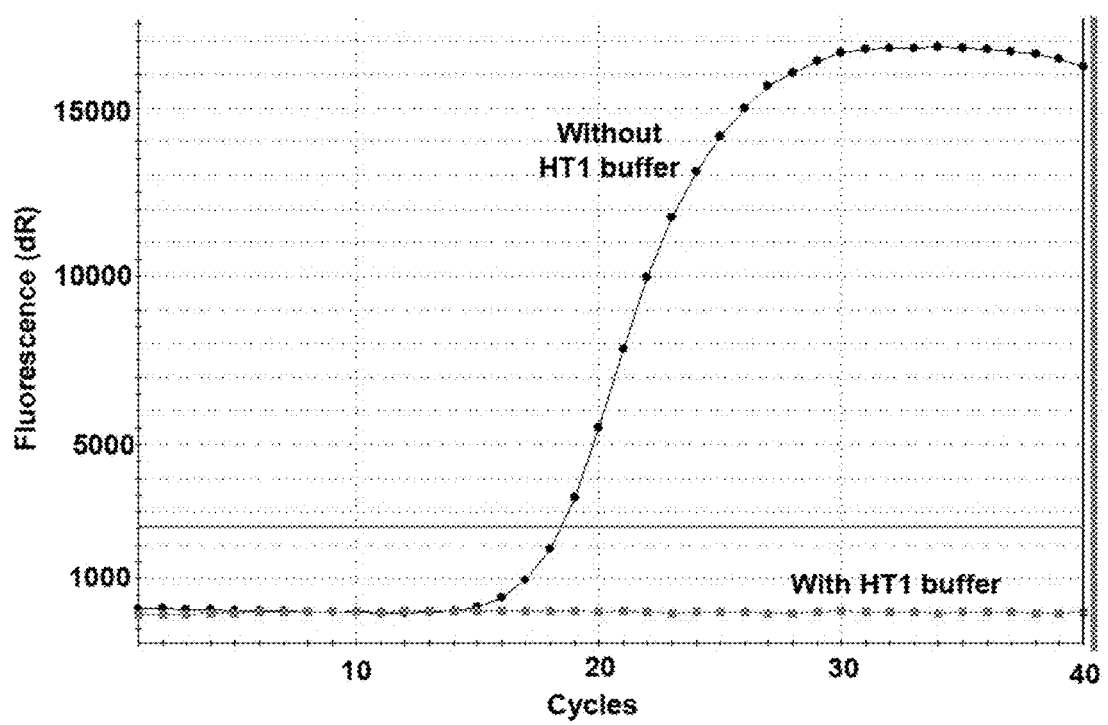
FIG. 3 graphically depicts experimental data obtained from nucleic acid amplification as described in Example 1.

As shown in FIG. 3, the reaction mixture not comprising HT1 buffer produced detectable amplicons whereas the reaction mixture comprising HT1 buffer did not yield detectable amplicons. Accordingly, data shown in FIG. 3 confirm the inhibitory nature of HT1 in nucleic acid amplification.

Figure 4B:
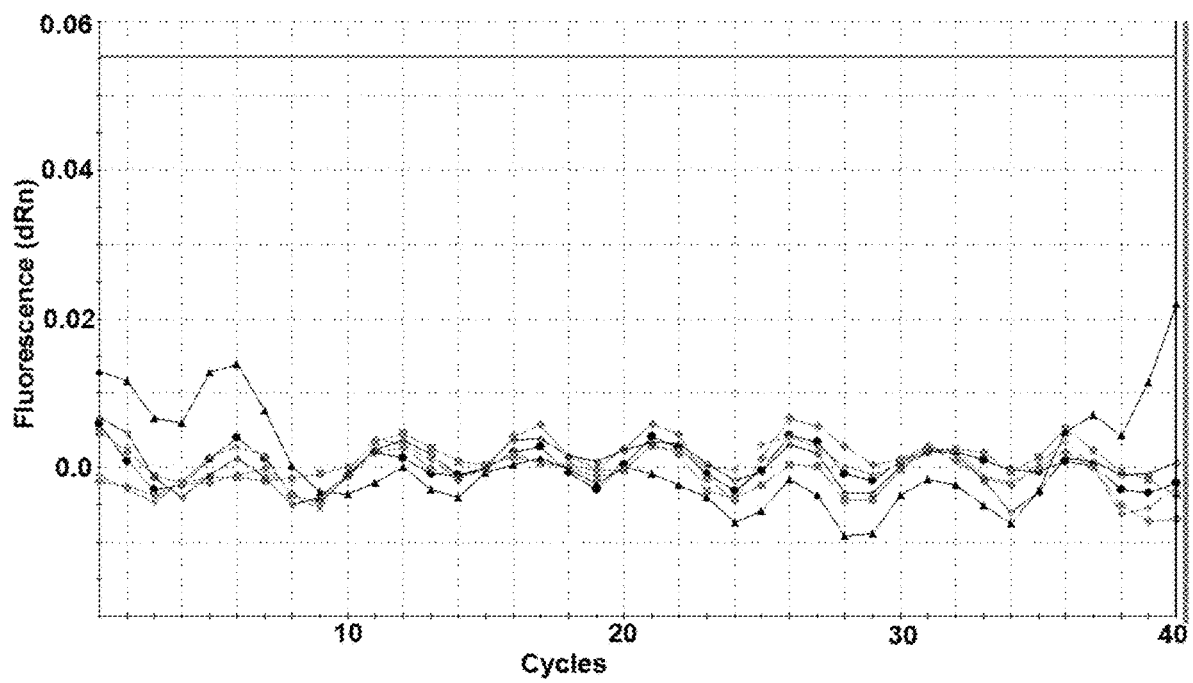
FIG. 4 (panel A) graphically depicts experimental data obtained from nucleic acid amplification as described in Example 1.

In a third set of experiments, amplification reaction mixture preparations each comprising a different concentration of nucleic acid template (ranging from 0.01 picomolar (pM) to 25 pM) were evaluated to determine the feasibility of amplifying a PhiX library control (Illumina) in the presence of HT1 buffer. The PhiX library control was suspended in HT1 buffer. A total of six reaction mixtures were evaluated, with each reaction mixture subjected to thermal cycling (e.g., 10 min. at 95° C., followed by 40 cycles of 95° C. for 30 seconds and 60° C. for 60 seconds) in a quantitative nucleic acid amplification reaction (e.g., qPCR) and optically monitored. Each reaction mixture comprised its respective concentration of template (in HT1 buffer), along with 67 mM Tris-HCl buffer, pH 8.8, 2 mM MgCl$_2$, 0.2 mM dNTP mix, 0.5× EvaGreen Dye, 16.6 mM ammonium sulfate, 10% glycerol and 0.05 U/μL Taq polymerase. A summary of the various non-template components in the reaction mixture and their concentrations are tabulated in FIG. 4 (panel B). The values in the table represent double the values of the concentrations in the reaction mixture. The results of each amplification experiment are graphically depicted in FIG. 4 (panel A). As shown in FIG. 4 (panel A), none of the reaction mixtures yielded detectable amplicons demonstrating that the HT1 buffer inhibited nucleic acid amplification.

Example 2: Monitoring Nucleic Acid Amplification

In a first set of experiments, two amplification reaction mixture preparations were evaluated to determine the feasibility of amplifying a plasmid comprising an insert from the GADPH gene in each mixture. In a second set of experiments, two amplification reaction mixtures comprising a PhiX library control (Illumina) were evaluated. Each reaction mixture was subjected to thermal cycling (e.g., 10 min. at 95° C., followed by 40 cycles of 95° C. for 30 seconds and 60° C. for 60 seconds) in a quantitative nucleic acid amplification reaction (e.g., qPCR) and optically monitored. One of the two reaction mixtures for each set of experiments included a 60 μg aliquot of plasmid or template in 1 μl of TE buffer, 10 μL of a reagents mix comprising multiple reagents necessary for nucleic acid amplification (e.g., a polymerase, dNTPs, etc.), 1 μL of a 5 μM primer mix and 8 μL of PCR grade water. The reagent mix included components shown in Table 2 at the concentrations indicated and was substantially free of potassium salt. The second reaction mixture in each set was identical to the first but also included 1 μL of HT1 buffer. The results of each amplification experiment are graphically depicted in FIG. 5 (GADPH) and FIG. 6 (PhiX).

Figure 5:
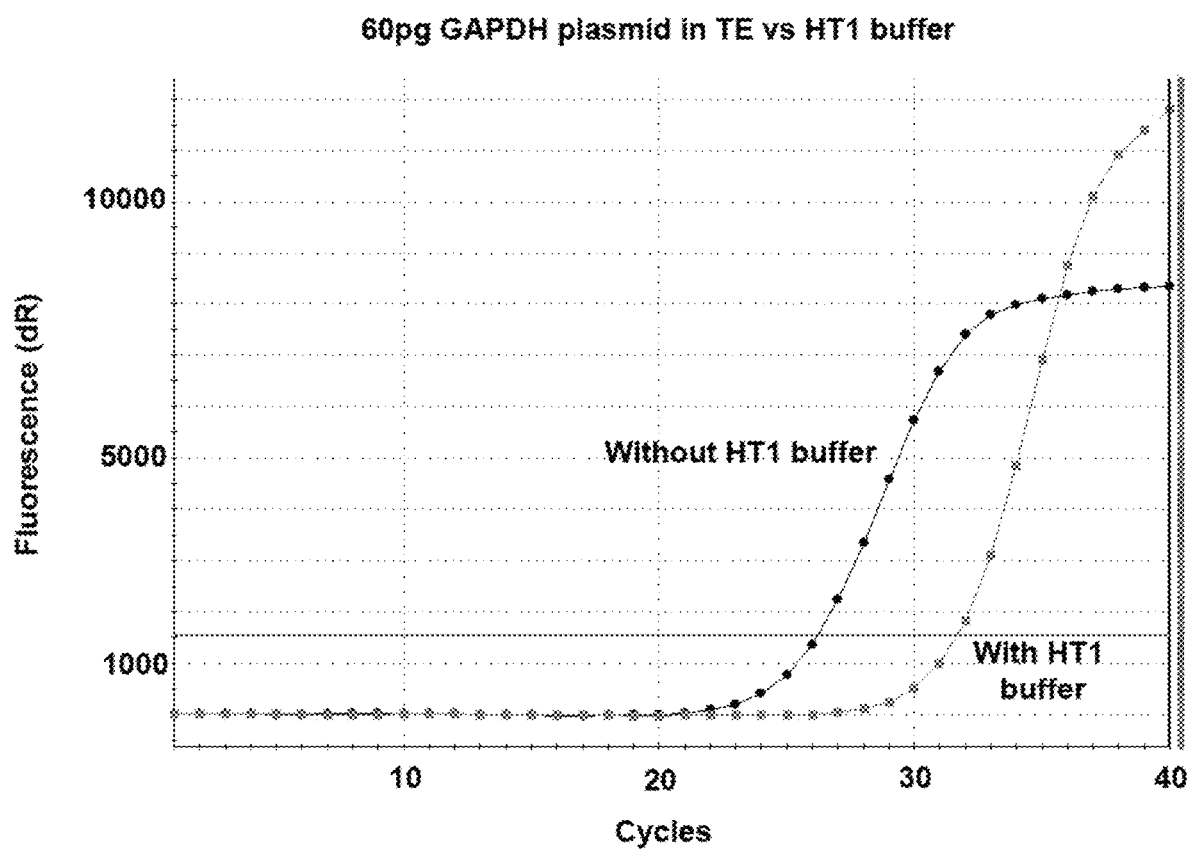
FIG. 5 graphically depicts experimental data obtained from nucleic acid amplification as described in Example 2.
Figure 6:
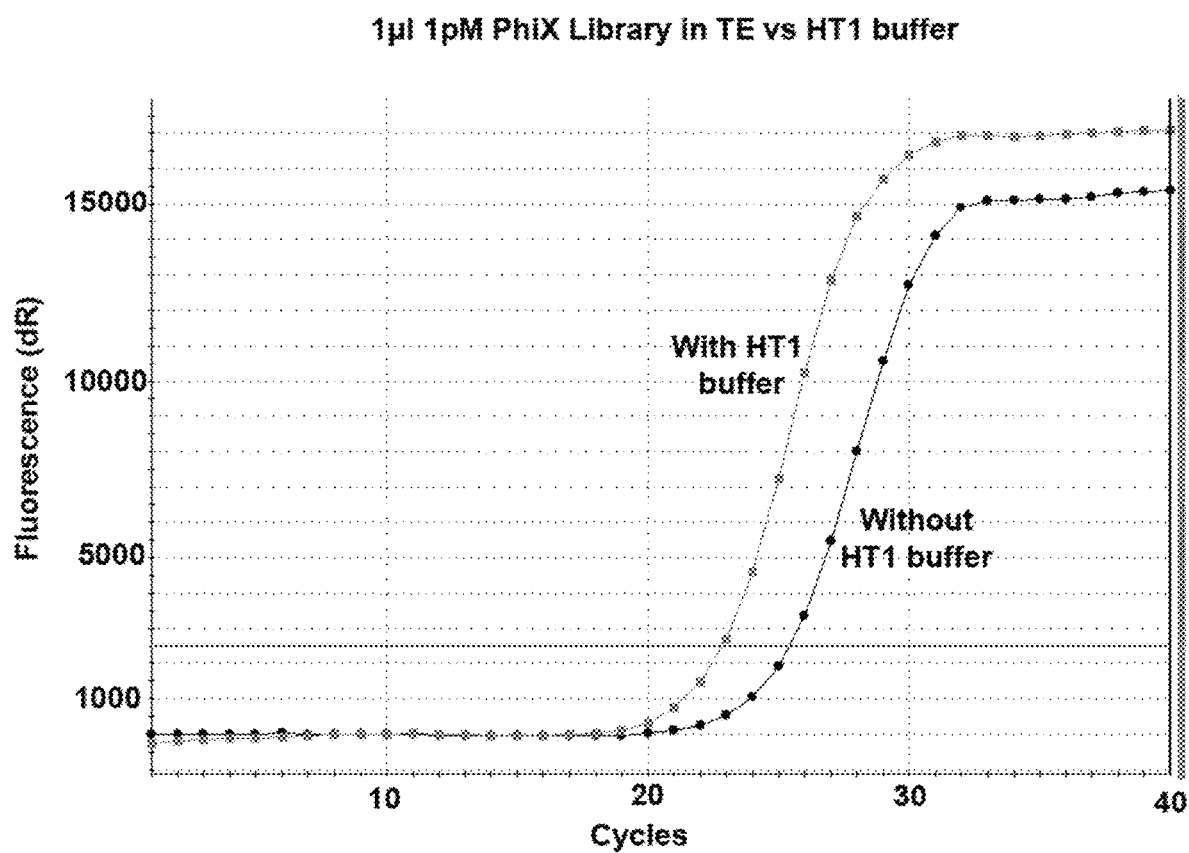
FIG. 6 graphically depicts experimental data obtained from nucleic acid amplification as described in Example 2.

As shown in FIG. 5 and FIG. 6, each of the reaction mixtures produced detectable amplicons, whether HT1 buffer was present or not. Accordingly, data shown in FIG. 5 and FIG. 6 confirm that the reaction mixture is suitable for amplification of a nucleic acid and quantitatively monitoring the generation of amplicons during amplification, even in the presence of HT1 buffer.

Example 3: Monitoring Nucleic Acid Amplification

Three amplification reaction mixture preparations were evaluated to determine the feasibility of amplifying a plasmid comprising an insert from the Beta Globin gene in each mixture. Each reaction mixture was subjected to thermal cycling (e.g., 10 min. at 95° C., followed by 40 cycles of 95° C. for 30 seconds and 60° C. for 60 seconds) in a quantitative nucleic acid amplification reaction (e.g., qPCR) and optically monitored. Each reaction mixture included an aliquot of plasmid in 1 μl of TE buffer, 10 μL of a reagents mix comprising multiple reagents necessary for nucleic acid amplification (e.g., a polymerase, dNTPs, etc.), 1 μL of a 5 μM primer mix and PCR grade water to a final volume of 20 μL. The reagent mix included components shown in Table 2 at the concentrations indicated and was substantially free of potassium salt. One reaction mixture included 1 μL of HT1 buffer, one included 2 μL of HT1 buffer and one did not include any HT1 buffer. The results of each amplification experiment are graphically depicted in FIG. 7.

Figure 7:
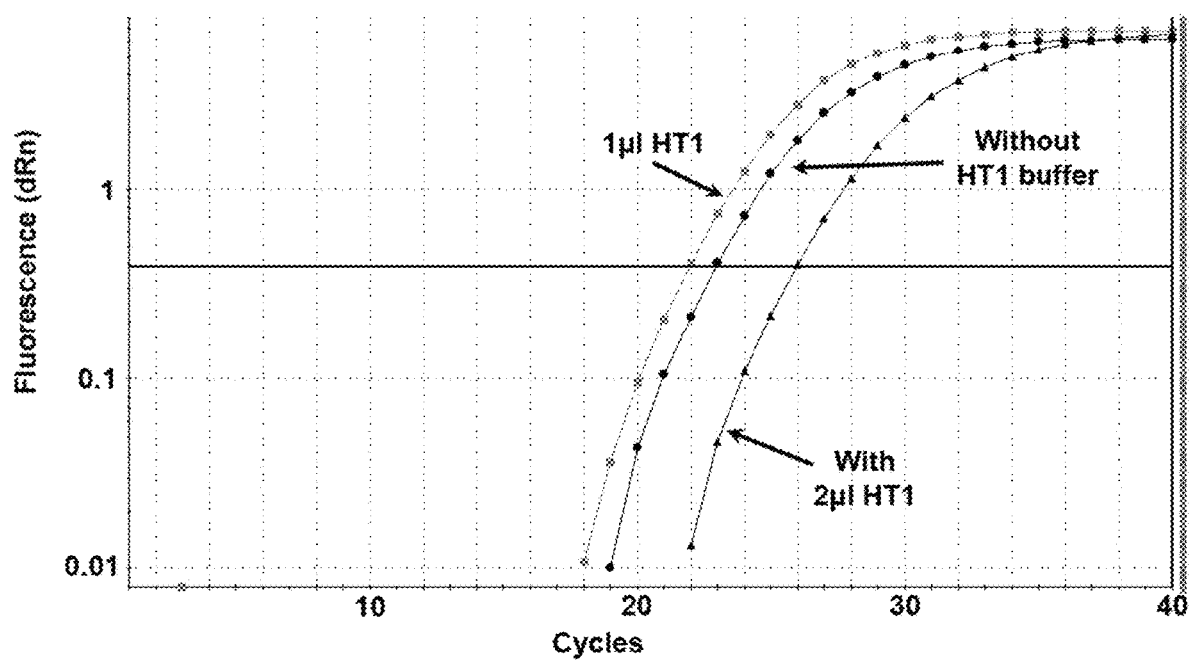
FIG. 7 graphically depicts experimental data obtained from nucleic acid amplification as described in Example 3.

As shown in FIG. 7, each of the reaction mixtures produced detectable amplicons at similar $C_t$ values (2 μl HT1→$C_t$=25.95, 1 μL HT1→$C_t$=21.92, No HT1→$C_t$=22.93), whether HT1 buffer was present or not or in varied concentration. Accordingly, data shown in FIG. 7 confirm that the reaction mixture is suitable for amplification of a nucleic acid and quantitatively monitoring the generation of amplicons during amplification, even in the presence of various amounts of HT1 buffer.

Example 4: Monitoring Nucleic Acid Amplification

Five amplification reaction mixture preparations were evaluated in duplicate (10 mixtures total) to determine the feasibility of amplifying a PhiX library control (Illumina) in each mixture. Each reaction mixture was subjected to thermal cycling (e.g., 10 min. at 95° C., followed by 40 cycles of 95° C. for 30 seconds and 60° C. for 60 seconds) in a quantitative nucleic acid amplification reaction (e.g., qPCR) and optically monitored. Each different reaction mixture included an aliquot of PhiX library control in 1 μl of HT1 buffer at a different concentration (25 pM, 10 pM, 1 pM, 0.1 pM or 0.01 pM), 10 μL of a reagents mix comprising multiple reagents necessary for nucleic acid amplification (e.g., a polymerase, dNTPs, etc.), 1 μL of a 5 μM primer mix, and 8 μL of PCR grade water. The reagent mix included components shown in Table 2 at the concentrations indicated and was substantially free of potassium salt. The results of each amplification experiment are graphically depicted in FIG. 8, with each data point depicting the average values for each duplicate pair of a single reaction mixture.

Figures 8A, 8B:
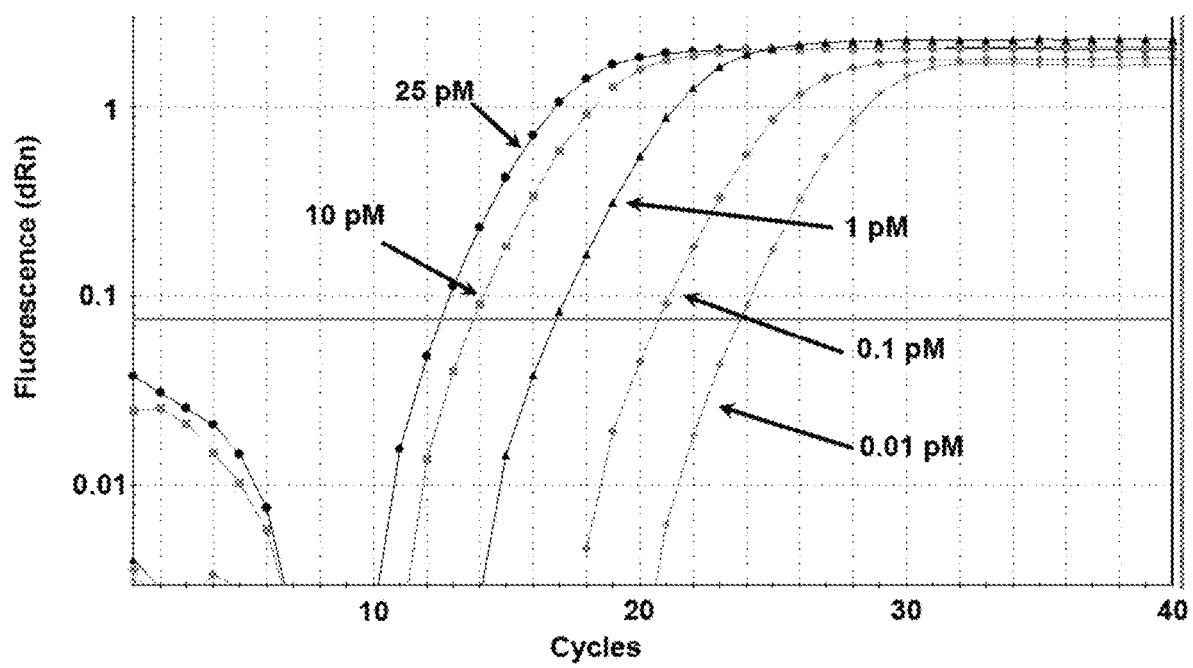
FIG. 8 (panel A) graphically depicts experimental data obtained from nucleic acid amplification as described in Example 4.

As shown in FIG. 8, each of the reaction mixtures produced detectable amplicons with increasing $C_t$ value at lower concentrations (25 pM→$C_t$=12.53, 10 pM→$C_t$=13.77, 1 pM→$C_t$=16.86, 0.1 pM→$C_t$=20.71, 0.01 pM→$C_t$=23.76). Accordingly, data shown in FIG. 8 confirm that the reaction mixture is suitable for amplification of a nucleic acid and quantitatively monitoring the generation of amplicons during amplification in the presence of HT1 buffer, at various amounts of template.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of amplifying one or more template nucleic acids present in a sample, said method comprising:
    (a) providing said sample comprising said one or more template nucleic acids, citrate, and sodium chloride;
    (b) using said sample to generate a nucleic acid amplification reaction mixture comprising: (i) said one or more template nucleic acids; (ii) reagents necessary for conducting a nucleic acid amplification reaction; (iii) said citrate; (iv) said sodium chloride; and (v) less than 10 mM potassium salt; and
    (c) performing said nucleic acid amplification reaction with said nucleic acid amplification reaction mixture to yield amplified products of said one or more template nucleic acids.

2. The method of claim 1, wherein said citrate comprises from 3 millimolar (mM) to 300 mM of sodium citrate.

3. The method of claim 1, wherein said nucleic acid amplification reaction mixture comprises from 30 mM to 3 molar (M) sodium chloride.

4. The method of claim 1, wherein said nucleic acid amplification reaction mixture is substantially free of potassium salt.

5. The method of claim 1, wherein said potassium salt is potassium chloride.

6. The method of claim 1, wherein said nucleic acid amplification reaction mixture further comprises ammonium salt.

7. The method of claim 6, wherein said ammonium salt is ammonium sulfate or ammonium chloride.

8. The method of claim 1, wherein said nucleic acid amplification reaction mixture is substantially free of ammonium salt.

9. The method of claim 6, wherein said nucleic acid amplification reaction mixture comprises less than 30 mM ammonium salt.

10. The method of claim 1, wherein said performing said nucleic acid amplification reaction comprises performing polymerase chain reaction (PCR) or quantitative PCR (qPCR).

11. The method of claim 10, further comprising determining a concentration of said one or more template nucleic acids present in said sample.

12. The method of claim 1, wherein said sample is directly introduced to said nucleic acid amplification reaction mixture without prior processing to a lower concentration of citrate, sodium chloride, or both.

13. The method of claim 1, wherein said nucleic acid amplification reaction mixture comprises HT1 buffer as supplied by Illumina.

14. The method of claim 1, wherein said performing said nucleic acid amplification reaction comprises: (i) denaturing said one or more template nucleic acids thereby generating one or more denatured template nucleic acids; (ii) annealing a primer to said one or more denatured template nucleic acids; (iii) extending said primer to generate one or more extended nucleic acids; and (iv) repeating (i)-(iii) one or more times using said one or more extended nucleic acids as templates, thereby generating said amplified products.

15. The method of claim 1, wherein said amplification reaction mixture further comprises a nucleic acid detection agent yielding a detectable signal, wherein an intensity of said detectable signal is proportional to an amount of said amplified products.

16. The method of claim 15, further comprising detecting said amplified products at a cycle threshold ($C_t$) of less than 35 cycles.

17. The method of claim 1, wherein said citrate, said sodium chloride, or both is present in said nucleic acid amplification reaction mixture in an amount that would otherwise inhibit said nucleic acid amplification reaction when performed in a nucleic acid amplification reaction mixture containing more than 10 mM potassium chloride.

18. The method of claim 1, wherein said reagents necessary for conducting a nucleic acid amplification reaction comprise a polymerase, nucleotides or analogues thereof, and primers to effect template-directed nucleic acid amplification.

19. A method for conducting a nucleic acid sequencing assay, said method comprising:
    (a) providing a sample comprising template nucleic acids, citrate, and sodium chloride;
    (b) quantifying an amount of template nucleic acids by performing a quantitative polymerase chain reaction (qPCR) in a nucleic acid amplification reaction mixture, wherein said qPCR directly utilizes said template nucleic acids, wherein said nucleic acid amplification reaction mixture contains said citrate, said sodium chloride, and less than 10 mM potassium salt; and
    (c) subjecting an appropriate amount of said template nucleic acids or derivatives thereof based on said quantifying of (b) to said nucleic acid sequencing assay, thereby generating sequences of said template nucleic acids.

20. The method of claim 19, wherein said qPCR directly utilizes said template nucleic acids such that said template nucleic acids in said sample are not processed to a lower concentration of citrate, sodium chloride, or both in said sample prior to said qPCR.

21. The method of claim 19, wherein said citrate is sodium citrate.

22. The method of claim 19, wherein said sample comprises a hybridization buffer.

23. The method of claim 22, wherein said hybridization buffer is HT1 buffer as supplied by Illumina.

24. The method of claim 19, wherein said citrate, said sodium chloride, or both is present in an amount that would otherwise inhibit quantitative polymerase chain reaction (qPCR) when performed in a nucleic acid amplification reaction mixture containing more than 10 mM potassium chloride.

25. The method of claim 19, wherein said nucleic acid amplification reaction mixture is substantially free of potassium salt.

26. The method of claim 19, wherein said nucleic acid amplification reaction mixture is substantially free of an ammonium salt.

27. The method of claim 19, wherein said nucleic acid amplification reaction mixture further comprises less than 30 mM ammonium salt.

28. The method of claim 27, wherein said ammonium salt is ammonium sulfate or ammonium chloride.

29. The method of claim 19, wherein said nucleic acid sequencing assay comprises a sequencing-by-synthesis reaction.

* * * * *